United States Patent [19]

Marinoff

[11] Patent Number: 4,520,815
[45] Date of Patent: Jun. 4, 1985

[54] HAND SUPPORTED SURGICAL INSTRUMENT

[76] Inventor: Gerald P. Marinoff, Eight Rockford Dr., West Nyack, N.Y. 10994

[21] Appl. No.: 506,427

[22] Filed: Jun. 21, 1983

Related U.S. Application Data

[63] Continuation-in-part of Ser. No. 389,842, Jun. 18, 1982, abandoned, which is a continuation-in-part of Ser. No. 199,693, Oct. 23, 1980, Pat. No. 4,340,059.

[51] Int. Cl.³ .............................................. A61B 17/00
[52] U.S. Cl. .................... 128/303 R; 128/305
[58] Field of Search ................. 128/305, 303 R, 305.1

[56] References Cited

U.S. PATENT DOCUMENTS

| | | | |
|---|---|---|---|
| 2,249,906 | 7/1941 | Longoria | 128/305 |
| 2,932,296 | 4/1960 | Sanders | 128/305 |
| 4,114,624 | 9/1978 | Haverstock | 128/303 R X |
| 4,336,805 | 6/1982 | Smirmaul | 128/305 X |
| 4,406,285 | 9/1983 | Villasenor et al. | 128/305 |

FOREIGN PATENT DOCUMENTS 8200584  3/1982  U.S.S.R. ............................. 128/305

Primary Examiner—Michael H. Thaler
Attorney, Agent, or Firm—Arthur Dresner

[57] ABSTRACT

A hand supported instrument for assisting in the formation of ophthalmological incisions includes a plate member which has a bottom surface adapted to rest upon the surface of the human eye. The bottom surface is curved so as to conform to the normally curved surface of the human eye. A longitudinally-oriented slot extends through the plate so as to serve as a guide for a knife blade intended to be positioned in the slot. The plate member also has a top surface which is spaced from the bottom surface by the thickness of the plate. In this manner, the top surface serves to limit the penetration of the knife blade through the slot. The thickness of the plate will vary from a minimum at one end of the slot to a maximum at the other end of the slot. In this fashion, the plate will serve as a template to control the depth of incision formed by the knife blade extending through the slot. A handle is connected to the plate at the thicker end of the plate so that it can be held in position for use.

13 Claims, 9 Drawing Figures

HAND SUPPORTED SURGICAL INSTRUMENT

CROSS REFERENCE

This is a Continuation-In-Part of prior application Ser. No. 06/389,842 filed June 18, 1982, now abandoned, which in turn was a Continuation-In-Part of application Ser. No. 199,693, filed Oct. 23, 1980, now U.S. Pat. No. 4,340,059, issued July 20, 1982.

FIELD OF THE INVENTION

This invention relates generally to the field of ophthalmological surgical instruments, and is particularly directed to a hand-held instrument to be used in forming incisions in the cornea. The invention may be used more specifically for the formation of radially oriented incisions in the cornea for correcting various eyesight deficiencies.

BACKGROUND OF THE INVENTION

It has been determined that myopia (or nearsightedness) and astigmatism are directly related to the curvature of the eye, and in particular of the cornea. Varying the degree of curvature of the cornea will, therefore, directly affect the degree of myopia and astigmatism. Recently, surgical procedures have been developed to vary the degree of curvature of the cornea. These procedures involve the placement of radial incisions, varying in length, about the cornea and extending up to or into the sclera. Further descriptions of this surgical technique can be found in articles by Professor S. Fyodrov; William D. Myers, M.D.; Leo Bores, M.D.; Ronald A. Schacher, M.D., et al; Ronald A. Schacher, M.D. alone; and Ronald A. Schacher, M.D. with Les Schacher, M.D.; all published in the Proceedings of the Keratorefractive Society for the meeting dated June 21, 1980.

Heretofore, the placement of the radially arranged incisions has been accomplished by free hand. Placement and positioning of the incisions has thus far, been the result of the surgeons' eye judgment. The success or failure of the technique to vary the curvature of the cornea and hence correct the eyesight deficiency will depend on a variety of dimensional factors associated with the incisions (i.e. "slits").

It has been found that the depth of the incisions is a critical factor in determining the degree of varying the curvature of the cornea.

The length of the incisions, the remaining optical zone and the angle of the incisions with respect to the surface of the cornea are also critical factors in performing a successful procedure. It has been found desirable that the angle of the incisions be 90° (i.e. perpendicular) with respect to the surface of the cornea. Perpendicular incisions will result in the thinnest possible scar width and thus minimal glare effect.

Incisions which are not perfectly radial will also have an effect on the results of such an operation.

Because control over the critical factors (i.e. spacing, length, depth and perpendicularity) are difficult, if not impossible to control when forming the incisions by free hand, the results to be expected from surgical procedures performed free hand cannot, therefore, be predicted. In addition, placement of corneal incisions by direct application of a knife blade to the surface of the cornea may cause excessive compression of the corneal wall thickness at the point of application and thus creates the danger of perforation.

It is, accordingly, a general object of the present invention to provide an ophthalmological surgical instrument, useful for forming radial incisions about the cornea which overcomes many of the disadvantages of using a free hand technique.

It is a more specific object of the present invention to provide a device to assist the surgeon in forming radial incisions in the cornea of the eye and which is capable of controlling the depth of the incision.

Another object of the invention is to provide a device of the foregoing type which is also capable of controlling the length of the radial incisions and therefore, the size of the optical zone.

Still a further object of this invention is to provide a device for assisting in the formation of radial incisions in the cornea which are perpendicular to the surface of the cornea.

Use of the present invention also minimizes the danger of perforating the cornea when forming such incisions by enlarging the area of contact to eliminate severe compression of the corneal wall.

The above objects, features and advantages, along with other objects, features and advantages of the present invention will become more apparent from the detailed description of the invention in conjunction with the accompanying drawings to be described more fully hereinafter.

SUMMARY OF THE INVENTION

The present invention is directed to a hand-held surgical instrument to facilitate making radial incisions required during surgical procedures to correct myopia and astigmatism.

The instrument of the present invention includes a plate member which has a bottom surface adapted to rest upon the surface of the human eye. The bottom surface is curved so as to conform to the normally curved surface of the human eye. A longitudinally-oriented slot extends through the plate so as to serve as a guide for a knife blade which may be positioned in the slot. The plate member also has a top surface which is spaced from the bottom surface by the thickness of the plate. In this manner, the top surface serves to limit the penetration of the knife blade through the slot. The thickness of the plate will vary from a minimum at one end of the slot to a maximum at the other end of the slot. In this fashion, the plate will serve as a template to control the depth of incision formed by the knife blade extending through the slot. A handle is connected to the plate at the thicker end of the plate so that it can be held in position for use.

The foregoing and other features of the present invention are more fully described with reference to the following drawings annexed hereto.

DESCRIPTION OF THE INVENTION

Figure 1A:
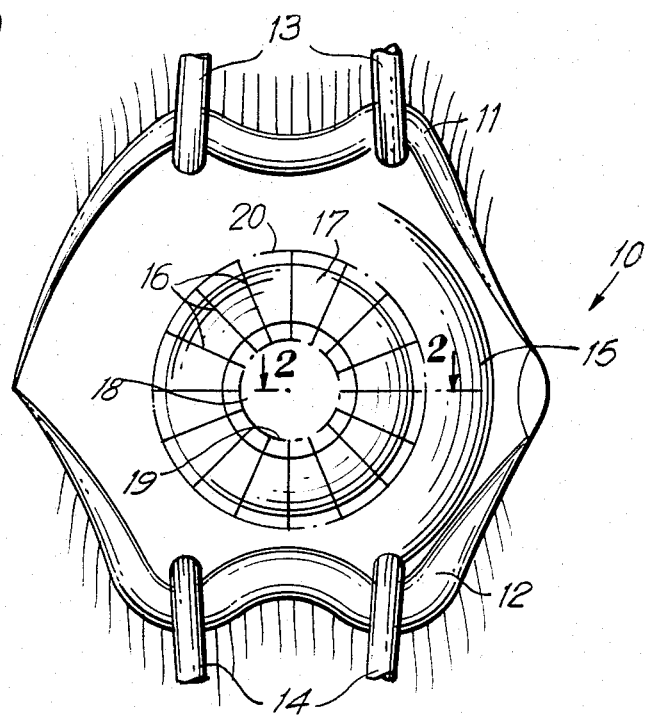
FIG. 1(a) is a plan view of the globe of the eye with eyelids shown in a retracted position and showing an example for locating the radial incisions to be performed with the present invention.

Referring now in greater detail to the accompanying drawings, FIG. 1(a) shows in plan view a representation of a human eye as prepared for surgery to correct myopia or astigmatism. The eye, indicated generally by reference numeral 10, has upper and lower eyelids 11 and 12, respectively, which are held in a retracted position by a pair of commonly used lid retractors 13, 14. These are commercially available, such as from the Storz Instrument Company under Catalog Nos. E-996, E-997, E-998 or E-1000. Retraction of the eyelids reveals a major portion of the globe 15 of the human eye so as to provide sufficient room for the surgeon to prepare the eye for the surgical procedure.

The particular placement, length and depth of the radial incisions will depend upon a number of objectives of the surgeon. However, placement of these incisions by free hand will rarely result in uniform results as to position length, radiality, perpendicularity or depth.

For purposes of explanation and understanding the present invention, and with reference to FIG. 1(a), the device of the present invention is intended for placement of a plurality of radial incisions 16 about the cornea 17. It has been found, and FIG. 1 illustrates, between six and sixteen incisions equi-distantly spaced about the cornea usually produces satisfactory results. More or fewer incisions may be placed depending upon the seriousness of the patient's condition and the degree of correction desired. An optical zone 18 is established by the surgeon and might be delineated by a slight score mark 19. The size of the optical zone 18 will depend on the refractive error, but will generally range from about 2.5–5.0 millimeters in diameter. The posterior border of the limbus is indicated generally by reference numeral 20. The length of the incisions 16 will depend upon the results to be achieved. However, incisions ranging in length from about ½ millimeter to about 6.0 millimeters, and preferably about 4.0 millimeters, have been found to be acceptable. Such incisions, if performed free hand, would require an unusually steady hand. Additionally, the angle of the incision, with respect to the surface of the cornea, might not be precisely perpendicular. It has been found that perpendicular incisions are preferable to those forming an acute angle with the surface of the cornea since such incisions will produce the thinnest possible scar, when viewed edge on, to thus reduce glare.

Figure 1B:
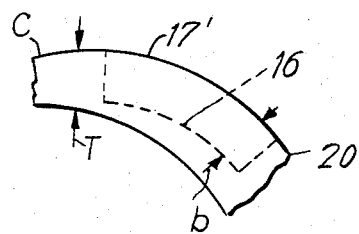
FIG. 1(b) is a cross sectional view taken through the cornea along lines 2—2 of FIG. 1(a) illustrating in dash lines a radial incision made by free hand.
Figure 1C:
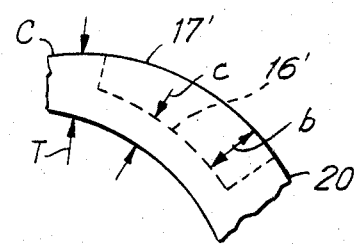
FIG. 1(c) is also a cross sectional view taken through the cornea along lines 2—2 of FIG. 1(a) illustrating in dash lines a radial incision made using the present invention.

Another factor believed to be critical in achieving successful results is to insure that the depth of the incisions vary over the length of the incisions so that the distance from the bottom of each incision to the endothelium remains constant. FIGS. 1(b) and 1(c) illustrate a section of cornea from its center C to the limbus 20. It is known that the thickness T of the cornea will increase from a minimum at its center C to a maximum at its posterior border 20. Therefore, as illustrated in FIG. 1(b), an incision 16 which is placed free hand by allowing a knife blade to penetrate up to a depth guard usually associated with such knives (such as bottom surface 52 of the knife shown in FIG. 2) will produce an incision having a depth "b" which is a constant distance from the surface 17'. However, as shown in FIG. 1(c) it is necessary to insure that the depth "b" increase from the center C toward the limbus 20 so that the distance "c" from the bottom of the incision to the endothelium 60 remains constant.

The use of the present invention makes the formation of these incisions a relatively simple matter regardless of the skill of the surgeon. The critical elements of length, depth and perpendicularity with the surface of the cornea can be precisely controlled as will be appreciated hereinafter.

In order to perform the incisions, the retractor 13 is positioned on the upper eyelid (the one toward the patient's forehead), while the retractor 14 is positioned at the patient's lower eyelid (the one adjacent the patient's cheek). After the incisions 16 are placed, using the present invention, the cornea 17 will have been flattened, thus correcting the myopia or astigmatism.

The device of the present invention, which will be used in order to perform the operation described in connection with FIG. 1, is illustrated in FIGS. 2 through 7.

Figure 2:
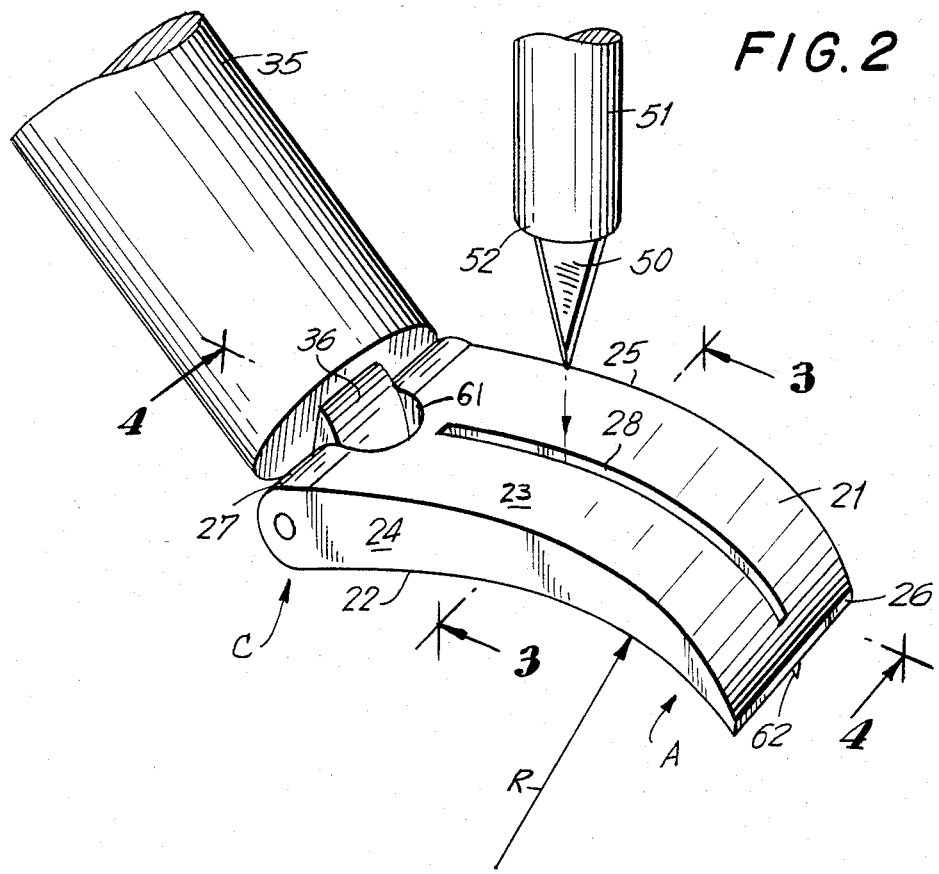
FIG. 2 is a perspective view illustrating one form of the present invention.
Figure 3:
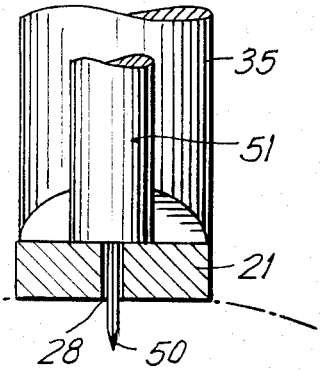
FIG. 3 is a sectional view taken along lines 3—3 of FIG. 2.
Figure 4:
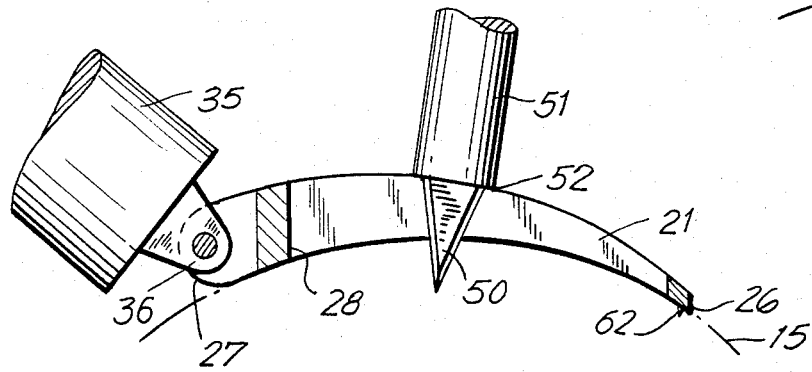
FIG. 4 is a sectional view taken along lines 4—4 of FIG. 2.
Figure 5:
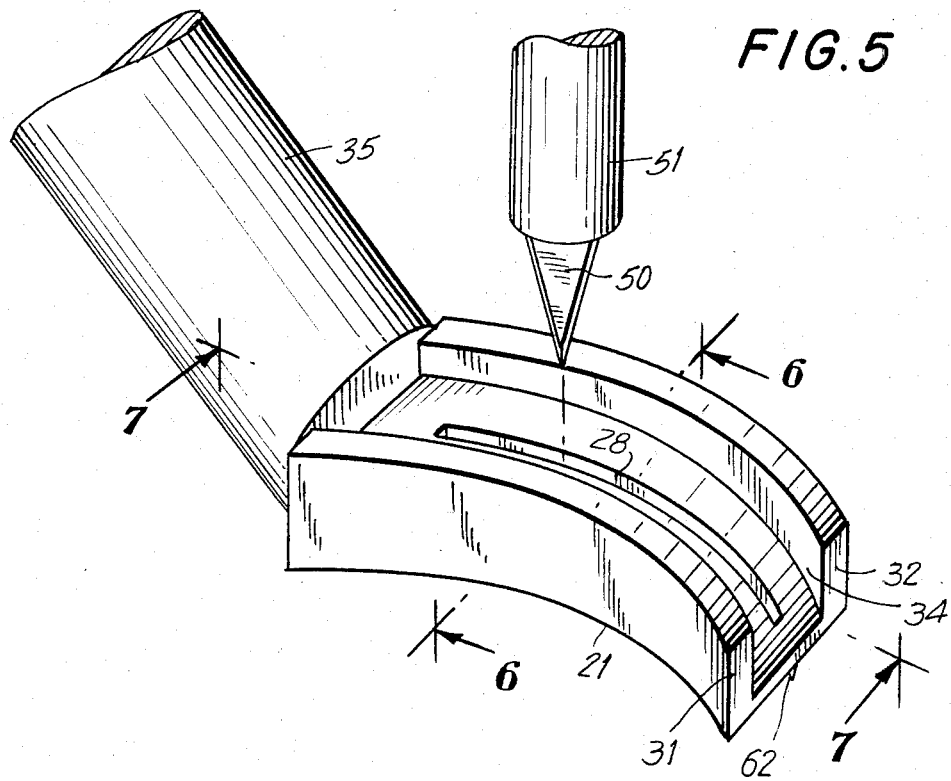
FIG. 5 is a perspective view illustrating another form of the present invention.
Figure 6:
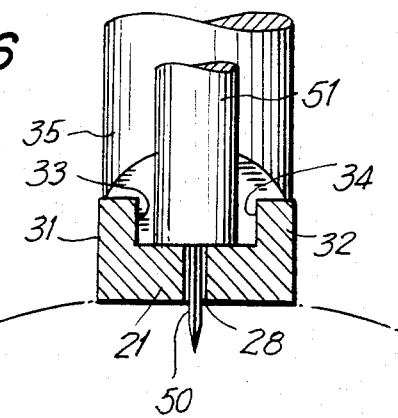
FIG. 6 is a sectional view taken along lines 6—6 of FIG. 5.

With reference to FIGS. 2-4 of the drawings, the present invention includes a plate member 21, having a bottom surface 22 and a top surface 23. The plate member is also formed by side walls 24 and 25 and ends 26 and 27.

The bottom surface 22 is curved so as to conform to the normal curvature of the human eye. In this manner, the plate member is adapted to rest upon the surface of the human eye, as is illustrated in FIGS. 3, 4 and 6, 7.

A longitudinally-oriented slot 28 extends through the plate 21 being open both at the top surface and at the bottom surface of the plate along its entire length. This slot thereby serves as a guiding channel for a knife blade 50 inserted through the slot to perform incisions in the cornea.

As noted above, it is known that the cornea is thinnest at its center and increases in thickness toward its periphery. In order to insure an incision of increasing depth from the center toward the periphery, to insure constant distance from the endothelium, plate 21 varies in thickness along its length and along the length of guide slot 28 to conform to and correspond in inverse proportion to the increase in thickness of the cornea. The radius of curvature R of the plate may range between 7 and 10 millimeters. The plate 21 may also be curved along its width having a radius of curvature R' (see FIG. 3). Plate 21 is thus curved to coincide with the generally spherical curvature of the cornea. The total increase in thickness from point A to point C is preferably between about 0.15–0.30 millimeters to thus account for the change in thickness of the cornea.

When plate 21 is placed for use on the surface of the human eye, it will thus conform to the shape of the cornea. The decrease in thickness of plate 21 from point C to point A will compensate for the increase in thickness of the cornea toward its periphery.

It can be seen from FIGS. 3 and 4 that plate 21 will serve to accurately control the depth of insertion of a knife blade extending through slot 28. Knife blade 50 is typically carried by a holder 51 which has a bottom 52. The bottom 52 will engage the top surface 23 of plate 21 to thereby limit the depth of insertion.

The top surface 23 thus acts to control the depth of insertion of the knife blade 50 since the holder 52 for the blade will ultimately contact top surface 23. The knife blades currently in use frequently include guards or other limits which will be used to engage the top surface 23 of the plate.

The width of slot 28 will be sufficient to accommodate most known knife blades without limiting their freedom of movement. The length of slot 28 should be at least 6 millimeters so that slits of up to this length can be made, but such slot can be between 3 and 7 millimeters long.

The thickness of the plate (and hence the depth of the slot 28) will be determined by the height of the knife blades to be used. This depth also serves to limit the angle at which the knife blade will penetrate the cornea. In order to provide additional means for insuring that the knife blade enters the cornea at a perpendicular angle, raised ridges 31 and 32 (see FIGS. 5-7) are provided on the surface 23 of the plate 21. The ridges 31 and 32 provide inner wall surfaces 33 and 34 respectively in order to provide a guide surface to engage the knife blade holder 51 and maintain position of the knife blade at a perpendicular angle.

A handle 35 is connected to the plate 21 at its thick end so that the surgeon can support the plate on the surface of the cornea with the thick end 27 positioned at the center of the cornea.

In order to assist the surgeon in being able to place the end 27 at the proper position at the center of the cornea, the plate 21 may be made of transparent material so that the surgeon can easily see through it for proper placement. Alternatively, a cut out 61 may be arranged at the thick end 27 to allow the surgeon to visually locate the center of the cornea.

At least one prong 62, which should be about ½ mm. long, is carried at the thin end of the plate. When the plate is placed in position for use the prong will partially penetrate the globe of the eye to help fix the position of the plate and prevent inadvertent movement.

Figure 7:
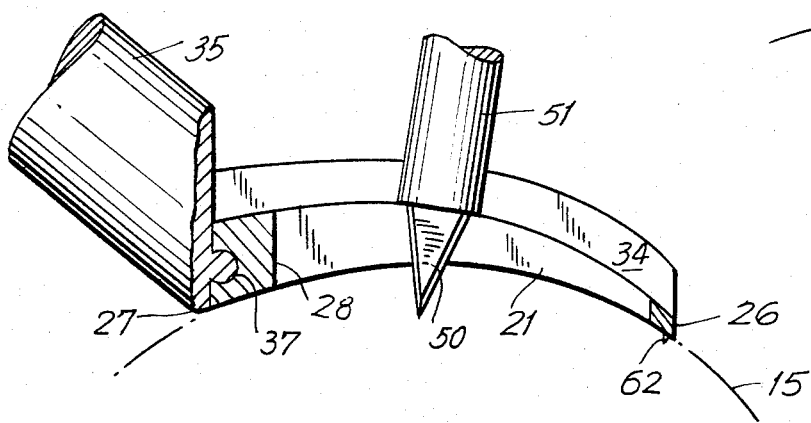
FIG. 7 is a sectional view taken along lines 7—7 of FIG. 6.

For convenience, the handle 35 can be attached to the thick end 27 by means of a hinge 36 (see FIGS. 2 and 3) so that its angle of connection to the plate can vary in accordance with the desires of the user. Alternatively, handle 35 may be removeably connected to plate 21, such as is shown in FIG. 7 using a ball and detent arrangement 37.

While the invention has been described and illustrated with respect to certain embodiments which produce satisfactory results, it will be understood by those skilled in the art, after understanding the purposes of the invention that various other changes and modifications may be made without departing from the spirit and scope of the invention, and it is, therefore, intended in the appended claims to cover all such changes and modifications.

What is claimed is:

1. A hand supported instrument for assisting in the formation of ophthalmological incisions comprising a plate member having opposing side walls, opposing end walls, the distance between said end walls forming a length dimension, the distance between said side walls forming a width dimension, said length dimension being greater than said width dimension, said plate member having a bottom surface adapted to rest upon the surface of the human eye, said bottom surface being curved so as to conform to the normally curved surface of the human eye, no more than one longitudinally oriented slot extending through said plate to serve as a guide for a knife blade positioned in said slot, said plate member having a top surface spaced from said bottom surface by the thickness of said plate member and serving as means for controlling penetration of said knife blade through said slot, the thickness of said plate member varying from a minimum at a first end of said slot to a maximum at the other end of said slot, and means comprising a handle connected to said plate member at an end wall thereof closest to said second end of said slot for holding said plate member in a desired position on the human eye.

2. The hand supported instrument according to claim 1 further comprising hinge means for connecting said handle to said plate member.

3. The hand supported instrument according to claim 2 wherein said handle is removably connected to said plate member.

4. The hand supported instrument according to claim 1 wherein the length of said slot is between 3 millimeters and 7 millimeters.

5. The hand supported instrument according to claim 4 wherein the width of said slot is sufficient to accommodate therein a knife blade.

6. The hand supported instrument according to claim 1 wherein the radius of longitudinal curvature of said bottom surface is between 7 and 10 millimeters.

7. The hand supported instrument according to claim 1 further comprising means on said top surface of said plate for supporting said knife blade at a desired angle to the surface of the eye.

8. The hand supported instrument according to claim 7 wherein said means for supporting said knife blade comprises a pair of raised guide rails extending parallel to said slot, one of said rails positioned on one side of said slot, the other of said rails positioned on the other side of said slot, whereby a knife blade extending through said slot is guided by said rails.

9. The hand supported instrument according to claim 1 further comprising means for visual positioning of said plate member.

10. The hand supported instrument according to claim 9 wherein said visual positioning means comprises a cut out through said plate at its thick end.

11. The hand supported instrument according to claim 9 wherein said visual positioning means comprises said plate member being transparent.

12. The hand supported instrument according to claim 1 further comprising fixation means carried on the bottom surface of said plate member for fixing the position of said plate member when in use.

13. The hand supported instrument according to claim 12 wherein said fixation means comprises at least one prong downwardly extending from the bottom surface of said plate member for partially penetrating the globe of the eye.

* * * * *